United States Patent [19]

Fruth et al.

[11] Patent Number: 5,175,370
[45] Date of Patent: Dec. 29, 1992

[54] PROCESS FOR THE PREPARATION OF SATURATED PRIMARY FATTY AMINES BY HYDROGENATION OF UNSATURATED FATTY ACID NITRILES

[75] Inventors: Anton Fruth, Garching; Julius Strauss, Altötting; Herbert Stühler, Burgkirchen, all of Fed. Rep. of Germany

[73] Assignee: Hoechst Aktiengesellschaft, Frankfurt am Main, Fed. Rep. of Germany

[21] Appl. No.: 806,585

[22] Filed: Dec. 12, 1991

[30] Foreign Application Priority Data

Dec. 14, 1990 [DE] Fed. Rep. of Germany ....... 4039936

[51] Int. Cl.⁵ ............................................. C07C 209/48
[52] U.S. Cl. ..................................... 564/493; 564/463
[58] Field of Search ................................ 564/493, 463

[56] References Cited

U.S. PATENT DOCUMENTS

| 3,163,676 | 12/1964 | Potts | 564/493 |
| 3,293,298 | 12/1966 | Szabo | 564/491 |
| 3,574,754 | 4/1971 | Specken | 564/493 |

FOREIGN PATENT DOCUMENTS

| 340848 | 11/1989 | European Pat. Off. | 564/493 |
| 372544 | 6/1990 | European Pat. Off. | 564/493 |
| 1024081 | 3/1966 | United Kingdom | 564/493 |

Primary Examiner—Carolyn Elmore
Assistant Examiner—Scott C. Rand

[57] ABSTRACT

According to the new process, the hydrogenation of unsaturated fatty acid nitriles or mixtures of unsaturated and saturated fatty acid nitriles is carried out in the liquid phase in the presence of nickel catalysts or cobalt catalysts. In a first reaction step the fatty acid nitrile, in the presence of ammonia, is treated with hydrogenation hydrogen until all the nitrile groups are hydrogenated to predominantly primary amino groups. After the ammonia content in the reaction mixture obtained from the first step has been adjusted to a value of at most 0.1 mol of ammonia per mole of fatty acid nitrile used, a second reaction step is used to hydrogenate the double bonds present to saturated bonds. The desired primary and saturated fatty amine is obtained in a very high yield and has an iodine number of at most 5.

8 Claims, No Drawings

PROCESS FOR THE PREPARATION OF SATURATED PRIMARY FATTY AMINES BY HYDROGENATION OF UNSATURATED FATTY ACID NITRILES

The invention relates to a process for the preparation of saturated primary fatty amines by hydrogenation of unsaturated fatty acid nitriles in the liquid phase in the presence of nickel catalysts or cobalt catalysts.

The preparation of primary fatty amines from fatty acid nitriles by hydrogenation of fatty acid nitriles in the liquid phase using nickel catalysts or cobalt catalysts has long been known. Thus in U.S. Pat. No. 3,293,298, a process is described for the preparation of primary alkylamines having 8 to 22 carbon atoms in which a corresponding alkyl nitrile is hydrogenated in the presence of a conventional nickel catalyst and in the presence of ammonia at a temperature of 120° to 150° C. and at a hydrogen pressure of 5 to 25 bar. To achieve a high yield of primary amine, the nickel catalyst is used in combination with a defined amount of a solid polar absorbent, such as aluminum oxide. As is apparent from the examples in which lauronitrile, stearonitrile and sebaconitrile are used as starting materials, saturated primary fatty amines are only obtained from saturated fatty acids by means of this process.

In U.S. Pat. No. 3,574,754 a process is described for the preparation of primary fatty amines from fatty acid nitriles, such as tallow fatty acid nitrile, oleonitrile and coconut fatty acid nitrile. In detail, the hydrogenation of these unsaturated fatty acid nitriles is accomplished by reacting the nitriles with hydrogen at a pressure of about 30 to 80 bar and a temperature of 50° to 200° C. in a single step in the presence of a conventional nickel or cobalt catalyst and in the presence of 0.5 to 8 mol of ammonia per mole of fatty acid nitrile, the hydrogenating hydrogen being added in portions to the reaction mixture comprising fatty acid nitrile, catalyst and the ammonia used. The hydrogen is preferably introduced at different sites of the reaction mixture, which is situated in a reaction zone, the introduction of the first portion of hydrogen being carried out close to the start of the reaction zone. This process likewise has the advantage that the easily obtainable and conventional nickel catalysts or cobalt catalysts can be used for the hydrogenation. The use of ammonia further results in the primary fatty amine being obtained in a relatively high yield, i.e. the undesired formation of by-products, that is secondary and tertiary fatty amine, being largely suppressed. However, a decisive disadvantage of this process is that double bonds present are not hydrogenated completely, if at all, to the corresponding saturated bonds. Thus, the examples of the U.S. Patent in question, in which the hydrogenation of tallow fatty nitrile is described, show that even though the reaction product does contain only small quantities of secondary and tertiary amine, its iodine number is very high (the iodine numbers given in Table I of the patent for the six examples are in the range from 38.1 to 50.5). The tallow fatty nitrile used did produce a primary tallow fatty amine, but not a primary and saturated amine; such a reaction product would clearly have a much lower iodine number.

During the preparation of saturated primary fatty amine by hydrogenation of unsaturated fatty acid nitrile it is therefore essential to exclude as far as possible the formation of secondary and tertiary amine, and furthermore to carry out the hydrogenation in such a manner that not only is the nitrile group hydrogenated to the primary amino group, but the double bonds present in the fatty acid nitrile are also hydrogenated to saturated bonds. The reaction product of the hydrogenation of unsaturated fatty acid nitriles (as a rule there are 1 to 3 olefinic bonds in the hydrocarbon group of the fatty acid nitrile) should therefore consist chiefly of the corresponding primary fatty amine and simultaneously show as low an iodine number as possible, that is an iodine number of at most 5, to indicate that the double bonds in the hydrocarbon moiety of the fatty acid nitrile have also been hydrogenated (the unsaturated starting nitrile generally has an iodine number of about 10 to 100).

It is accordingly the object of the invention to provide a process for the hydrogenation of unsaturated fatty acid nitriles using conventional and easily obtainable nickel or cobalt catalysts, by which primary and saturated fatty amine is obtained, i.e. by which therefore the olefinic bond(s) in the unsaturated fatty acid nitrile and also the nitrile group are completely hydrogenated, the formation of undesired by-products, secondary and tertiary amine, proceeding only to a negligible extent, if at all. The new process for the preparation of saturated primary fatty amines from the corresponding unsaturated fatty acid nitriles is therefore intended to supply primary and saturated fatty amine in very high yield and with an iodine number of at most 5.

The process according to the invention for the preparation of saturated primary fatty amines by hydrogenation of unsaturated fatty acid nitriles in the liquid phase in the presence of nickel catalysts or cobalt catalysts comprises a first reaction step in which the nitrile group of the fatty acid nitrile is hydrogenated to the primary amino group by reaction of the fatty acid nitrile with hydrogen in the presence of 0.1 to 10% by weight of said catalyst, preferably 0.5 to 5% by weight of said catalyst, relative to the fatty acid nitrile, and in the presence of 0.3 to 3 mol, preferably 0.5 to 1.5 mol of ammonia per mole of fatty acid nitrile, at a temperature of 80° to 160° C., preferably 100° to 140° C., and a pressure of 10 to 50 bar, preferably 20 to 40 bar, after which the ammonia content in the hydrogenation reaction mixture is reduced to a value of 0.1 to 0 mol, preferably of 0.05 to 0 mol, per mole of fatty acid nitrile used, and a second reaction step in which the double bonds in the fatty acid nitrile are hydrogenated to saturated bonds by reaction of the reaction mixture mentioned, having an ammonia content of at most 0.1 mol, preferably at most 0.05 mol, per mole of fatty acid nitrile used, with hydrogen at a temperature of 80° to 160° C., preferably 100° to 140° C., and a pressure of 1 to 40 bar, preferably 1 to 25 bar, until primary and saturated fatty amine is present.

In the process according to the invention, the hydrogenation is thus carried out in two steps separate from each other. In the first step the —C≡N group is hydrogenated to the —CH$_2$—NH$_2$ group, and in the second step the unsaturated hydrocarbon group is hydrogenated to the saturated hydrocarbon group. During this procedure, defined reaction conditions are maintained in each case. Of these conditions, the differing quantities of ammonia in the two reaction steps are particularly noteworthy. In the first step the hydrogenation (first hydrogenation) is carried out in the presence of a relatively large amount of ammonia, whereas in the second step (second hydrogenation) ammonia is present only in a much smaller amount, if at all.

The starting material for the process according to the invention is unsaturated fatty acid nitriles having 8 to 22 carbon atoms, preferably 12 to 18 carbon atoms, or their mixtures or mixtures of these fatty acid nitriles and up to 90% by weight, preferably up to 60% by weight, of saturated fatty acid nitriles of the chain length mentioned, the percentages by weight being based on the sum of the weights of the saturated and unsaturated fatty acid nitriles. The fatty acid nitriles used are thus unsaturated fatty acid nitriles having 8 to 22 carbon atoms, preferably 12 to 18 carbon atoms, and preferably having 1 to 3 (conjugated or preferably isolated) double bonds or their mixtures, which can be prepared by known methods from the corresponding fatty acids. Just as suitable are also mixtures of unsaturated and saturated nitriles, preferably those prepared from fatty acids of naturally occurring fats and oils, examples of which are the acids from tallow fatty acid, coconut fatty acid, palm kernel fatty acid, fish fatty acid, cottonseed oil fatty acid, rapeseed oil acid, rice oil acid, sunflowerseed oil acid and soybean oil acid. These mixtures can contain, in addition to the unsaturated fatty acid nitriles, up to 90% by weight, preferably up to 60% by weight, of saturated fatty acid nitriles having 8 to 22 carbon atoms, preferably having 12 to 18 carbon atoms. The process according to the invention is thus applicable to unsaturated fatty acid nitriles having 8 to 22 carbon atoms, preferably 12 to 18 carbon atoms, which contain 0 to 90% by weight, preferably 0 to 60% by weight, of saturated fatty acid nitriles having 8 to 22 carbon atoms, preferably 12 to 18 carbon atoms. A particularly preferred starting material is tallow fatty nitrile, which is isolated from animal tallow, and comprises about 40 to 75% by weight of unsaturated $C_{16}$ nitrile and in particular $C_{18}$ nitrile (1 to 3 double bonds in the carbon chain) and about 25 to 60% by weight of saturated $C_{14}$, $C_{16}$, and $C_{18}$ nitriles. The nitrile mixtures originating from natural fats can also contain the higher and lower even-numbered homologs in small amounts. The numbers given for the carbon atoms include the nitrile group carbon. The fatty acid nitriles in question have iodine numbers in the range from 10 to 100. Thus the tallow fatty nitriles mentioned normally have an iodine number of 30 to 60 (the iodine number is known to indicate the consumption in g of iodine per 100 g of substance).

The process according to the invention, on use of the fatty acid nitriles mentioned, accordingly gives a reaction product comprising saturated primary fatty amines having 8 to 22 carbon atoms, preferably 12 to 18 carbon atoms, in the alkyl chain (the alkyl chains may be identical or different).

The process according to the invention is carried out (first reaction step) by introducing the unsaturated fatty acid nitrile or unsaturated fatty acid nitriles or the mixture of unsaturated and saturated nitriles into an autoclave equipped with a heating/cooling jacket and a highly effective stirrer. A reactor can also be used in which the contents are continuously circulated by pump. Installed in the circulation line are a heat exchanger having heating and cooling ability and an injector which continuously draws in gas from the reactor. The reaction vessels have in addition devices for the introduction and removal of gases, for filling and emptying, and for monitoring and regulating the pressure and temperature. As far as is practicable, the fatty acid nitrile used is introduced in the molten state. The reaction vessel further contains the catalyst intended for the hydrogenation of the nitrile. Suitable catalysts are nickel catalysts and cobalt catalysts which can be doped with traces of other metals, examples of which are calcium, barium, iron, manganese and molybdenum, and which may be used in the form of powder contact catalysts, supported catalysts or Raney catalysts. Suitable materials for powder contact catalysts and supported catalysts are for example aluminum oxide, silica gel, kieselguhr and pumice stone. Preference is given to nickel catalysts, particularly in the form of Raney nickel. The catalysts mentioned are added in an amount of 0.1 to 10% by weight, preferably in an amount of 0.5 to 5% by weight, percentages by weight being relative to the weight of the fatty acid nitrile used (the percentages by weight mentioned are obviously based on the elements nickel and cobalt, and therefore do not include the support material, for example).

It is advantageous for the starting mixture to be substantially free from water. The removal of any water present can be achieved for example by heating the starting mixture (fatty acid nitrile and catalyst) to a temperature of over 100° C., preferably to a temperature of 120° to 130° C., and flushing it with nitrogen in a known manner with good stirring.

To the mixture of fatty acid nitrile and catalyst in the reaction vessel is added ammonia (liquid) in a quantity of 0.3 to 3 mol, preferably of 0.5 to 1.5 mol, per mole of fatty acid nitrile used. The hydrogenation in the first step of the process according to the invention, i.e. the hydrogenation of the nitrile group, is accomplished in the presence of the stated quantity of ammonia at a pressure (total pressure) of 10 to 50 bar, preferably 20 to 40 bar, and at a temperature from 80° to 160° C., preferably from 100° to 140° C. The higher of the stated pressure and temperature values are selected when a relatively short reaction time is desired. The supply of hydrogen for hydrogenation into the reaction vessel can be begun before or after heating up to the reaction temperature (it is expedient to deliver the first quantity of hydrogen before the heating). The hydrogen for hydrogenation can be introduced continuously or in portions, with maintenance of the stated temperature and stated pressure in the reaction vessel, means obviously being provided to ensure intimate contact with the reaction mixture (for example by vigorous stirring, constant pumped circulation or circulation of gas). The hydrogen for hydrogenation is passed in in such a quantity and for such a period, that substantially all the —C≡N groups are hydrogenated. This is the case when at most only 2% by weight of the nitrile used, preferably at most 0.5% by weight, are detectable. The —C≡N groups have been hydrogenated substantially to primary amino groups. Olefinic double bonds may also have been hydrogenated in the first step (this hydrogenation generally covers—as shown by determination of the iodine number—at most up to 20 mol % of the total double bonds present). In any case, the decisive factor is that after the hydrogenation procedure in the first step, there are practically no more nitrile groups in the reaction mixture. The time for this first hydrogenation is as a rule 2 to 4 hours, depending chiefly on the catalyst and the reaction temperature.

After completion of the hydrogenation in the first step of the process according to the invention, the ammonia present is removed to a value of at most 0.1 mol, preferably at most 0.05 mol, per mole of fatty acid nitrile used. The removal of the ammonia from the reaction mixture (and also from the gas space of the reaction vessel), subsequently to the first hydrogenation, can be accomplished for example simply by pressure reduction. Adjusting the mixture to the stated ammonia contents can also be carried out, for example, by scrubbing with water or with the aid of other absorption agents. The temperature at which this process occurs is not in itself critical and can be adapted to circumstances. The reduction in pressure mentioned is thus carried out at a temperature from about 80° to 130° C. Rapid cooling of the reaction mixture is avoided for the reason that the reaction mixture must possibly be heated up again for the further hydrogenation. It is preferred for the reaction mixture present after the first hydrogenation to be practically completely freed from the ammonia present. The procedure used for the removal of the ammonia (scrubbing by gas circulation, pressure reduction and the like) is not critical.

After adjustment to the stated ammonia contents of 0 to 0.1 mol, preferably 0 to 0.05 mol, per mole of fatty acid nitrile used, in the reaction mixture after the first hydrogenation, the second hydrogenation is carried out, i.e. the hydrogenation of the olefinic double bonds still present in the reaction mixture. This hydrogenation is carried out at a pressure of 1 to 40 bar, preferably 1 to 25 bar, and a temperature of 80° to 160° C., preferably 100° to 140° C. If the reaction mixture has been cooled after the first hydrogenation, it is then to be heated up again to the reaction temperature. The second hydrogenation is generally carried out at about the same temperature as the first hydrogenation. The pressure during the second hydrogenation can be substantially lower in comparison with the first hydrogenation. The second hydrogenation can thus be carried out at atmospheric pressure (1 bar), that is without applied pressure. In this case, any entry of air into the reaction vessel should be prevented by appropriate means, for example a slight overpressure. The decisive characteristic of the second hydrogenation compared with the first hydrogenation is, however, as has already been mentioned, that no, or only very little, ammonia is present. As far as the amount of catalyst for the second hydrogenation is concerned, the quantity of catalyst used initially suffices as a rule, even when one hydrogenation has already been carried out with it. The hydrogenation itself can be carried out analogously to the first hydrogenation. After the desired reaction temperature is attained, the hydrogen for hydrogenation is thus introduced. It can be delivered continuously or in portions, with maintenance of the reaction temperature. The hydrogen for hydrogenation is supplied in such a quantity and for such a period that practically no double bond, if any, is detectable any more (iodine number determination). The time for the second hydrogenation is in the range from preferably 1 to 4 hours. It depends, just as the first hydrogenation does, on the catalyst and the reaction temperature. As a rule, enough catalyst is used in the first reaction step so that the second hydrogenation is completed in the time mentioned. However, as the time required for the second hydrogenation does not depend only on the catalyst and the temperature, but also on the amount of ammonia that may be present (a greater amount of ammonia, for an identical catalyst and identical reaction temperature, results in a longer reaction time), fresh catalyst is added in the second step if relatively little catalyst was used in the first step. After the second hydrogenation, the desired primary and saturated fatty amine is present.

If separation of the primary saturated fatty amine from the catalyst used is required, this can be achieved for example simply by decanting or filtering. The recovered catalyst is also suitable for further hydrogenations according to the invention.

The process according to the invention has a number of advantages. It is simple to carry out. It gives the desired primary saturated fatty amines having an iodine number of less than 5 and in a high yield, i.e. with negligible quantities of the secondary and tertiary fatty amine by-products. The high yield and purity of the fatty amine are achieved in a relatively short reaction time. The process according to the invention is thus distinguished by favorable economics. The primary saturated fatty amine obtained is moreover of pale color, and the good color is maintained for example even in the case of alkoxylation reactions. The primary saturated fatty amines in question are known to be valuable products for the preparation of detergents, herbicides, disinfectants, antistatic agents, anticaking agents, textile finishes and flotation agents.

The invention will now be illustrated in greater detail by means of examples.

EXAMPLE 1

800 g (3.2 mol) of oleonitrile having an iodine number of 88 and 40 g of Raney nickel (i.e. 5% by weight of nickel, relative to oleonitrile) are introduced into a 2-l stirred autoclave. After flushing with nitrogen, 70 g (4.1 mol) of liquid ammonia are added (that is 1.3 mol of $NH_3$ per mole of oleonitrile). The mixture is heated to 130° C. with stirring. At this temperature hydrogen is injected to a pressure of 35 bar, and this pressure is maintained by further supply of hydrogen using a pressure regulator. After a reaction time of 2½ hours, no more hydrogen is taken up, indicating completion of the hydrogenation of the nitrile group of the oleonitrile. The stirred autoclave is then completely depressurized, and the autoclave contents cooled to 60° C. are transferred to an open 2-l stirred flask. The primary oleylamine obtained has the following analytical values:
  primary nitrogen in equivalent percent: 96.7
  non-primary nitrogen in equivalent percent: 3.3
  residual content of oleonitrile in percent by weight: 0.3
  iodine number: 73

By means of the mentioned depressurization and transfer of the reaction mixture (including catalyst) to the 2-l stirred flask the ammonia content of the reaction mixture is only 1 g (0.06 mol), that is 0.019 mol of $NH_3$ per mole of oleonitrile used. The second hydrogenation (second reaction step) is carried out by first flushing the contents of the open stirred flask with nitrogen, and then heating the mixture to 140° C. and maintaining it at this temperature. Introduction of hydrogen is begun during the heating, at a rate of 55 l of hydrogen per hour. This supply of hydrogen is continued for 3½ hours. After this time the atmospheric pressure hydrogenation of the double bonds in the oleyl moiety of the primary oleylamine is completed. A saturated primary amine (stearylamine) is present having the following analytical values:
  primary nitrogen in equivalent percent: 96.0
  non-primary nitrogen in equivalent percent: 4.0
  residual content of oleonitrile in percent by weight: <0.1 iodine number: 4

EXAMPLE 2

700 g. (3.5 mol) of coconut fatty acid nitrile having an iodine number of 10 and 30 g of Raney nickel, filtered off from the reaction mixture after the second hydrogenation in Example 1 (i.e. 4.3% by weight nickel, relative to the coconut fatty acid nitrile), are introduced into a 2-1 stirred autoclave. After flushing with nitrogen and addition of 90 g (5.3 mol) of liquid ammonia (i.e. 1.5 mol $NH_3$ per mole of coconut fatty acid nitrile) hydrogen is injected to a pressure of 30 bar, after which the mixture is heated to 135° C. with stirring. At this temperature, hydrogen is repeatedly passed in up to a maximum pressure of 40 bar until no further fall in pressure is detectable. This is the case after 3¼ hours. The primary coconut fatty amine formed has the following analytical values:

primary nitrogen in equivalent percent: 97.1
non-primary nitrogen in equivalent percent: 2.9
residual content of coconut fatty acid nitrile in percent by weight: 0.1
iodine number: 9

The ammonia is removed from the autoclave and from the first hydrogenation reaction mixture by completely depressurizing the autoclave and flushing its contents at 80° C. with nitrogen until the ammonia content in the reaction mixture is only 0.5 g (0.03 mol) (i.e. 0.009 mole $NH_3$ per mol of coconut fatty acid nitrile used). The autoclave is then flushed free of nitrogen using hydrogen, and then hydrogen is injected to a pressure of 6 bar. After turning on the stirrer and heating the mixture to 135° C., hydrogenation of the double bonds is accomplished by hydrogen used constantly replenishing the consumed hydrogen by means of a pressure regulator and maintaining the cited pressure of 6 bar. After 3½ hours the reaction is completed. The saturated primary amine obtained has the following analytical values:

primary nitrogen in equivalent percent: 96.5
non-primary nitrogen in equivalent percent: 3.5
residual content of coconut fatty acid nitrile in percent by weight: <0.1
iodine number: 3

EXAMPLE 3

35 kg (140 mol) of tallow fatty nitrile together with 0.88 kg of Raney nickel (i.e. 2.5% by weight of nickel, relative to tallow fatty nitrile) and 1.75 kg (102.9 mol) of ammonia (i.e. 0.74 mol $NH_3$ per mole of tallow fatty nitrile) are introduced into a reactor previously flushed using nitrogen. The reactor is equipped so that its contents can be pumped back into the reactor through a heat exchanger and an injector. The injector simultaneously draws in gas from the reactor and mixes it intensively with the liquid. The tallow fatty nitrile comprises 65% by weight of fatty acid nitrile having 18 carbon atoms and 35% by weight of fatty acid nitrile having essentially 14 and 16 carbon atoms, where 50% by weight is unsaturated fatty acid nitrile having 1 to 3 double bonds and 50% by weight is saturated fatty acid nitrile; the iodine number is 57.

The reactor pump is turned on and the reaction mixture is heated up to 125° C. A pressure of 22 bar is established. Hydrogenation hydrogen is then constantly supplied to the system, where 28 bar and 130° C. are not exceeded (the heat of reaction is dissipated by the heat exchanger mentioned to the product loop). The uptake of hydrogen is completed after 3 hours. A primary tallow fatty amine has been formed having the following characteristics:

primary nitrogen in equivalent percent: 97.2
non-primary nitrogen in equivalent percent: 2.8
residual content of tallow fatty nitrile in percent by weight: 0.2
iodine number: 45

The reactor is then depressurized to 2 bar with the reactor pump running and at a temperature of 130° C. to remove the ammonia; by this means the ammonia content in the system (in the reaction mixture) is reduced to 0.13 kg (7.6 mol) (i.e. 0.05 mol of $NH_3$ per mole of tallow fatty nitrile used). The reaction mixture, which was maintained at 130° C., is then again pressurized using hydrogen up to a pressure of 25 bar, and is maintained at this pressure by constant supply of hydrogen (this is the second reaction step or the second hydrogenation). The hydrogenation of the double bonds is completed after 3 hours. A hardened tallow fatty amine is obtained having the following characteristics:

primary nitrogen in equivalent percent: 96.6
non-primary nitrogen in equivalent percent: 3.4
residual content of tallow fatty nitrile in percent by weight: <0.1
iodine number: 4

EXAMPLE 4

30 kg (120 mol) of tallow fatty nitrile of Example 3 are placed in the reactor of example 3 made inert by nitrogen, together with 0.6 kg of nickel supported catalyst, comprising 50% by weight of nickel and 50% by weight of silicon dioxide as support material (that is 1.0% by weight of nickel, relative to tallow fatty nitrile) and 2 kg (117.6 mol) of ammonia (that is 0.98 mol of $NH_3$ per mole of tallow fatty nitrile). The nickel catalyst has already been used three times in the two-step reaction described.

After the reactor pump is turned on, the reaction mixture is heated up to 120° C., after which hydrogen is injected to a pressure of 30 bar. The supply of hydrogenation hydrogen is continued, where 30 bar and 125° C. are not exceeded. The uptake of hydrogen is completed after 2.5 hours. A primary tallow fatty amine has been formed having the following characteristics:

primary nitrogen in equivalent percent: 98.2
non-primary nitrogen in equivalent percent: 1.8
residual content of tallow fatty nitrile in percent by weight: 0.2
iodine number: 48

The removal of the ammonia from the system is accomplished by passing the gas phase through a water-driven adsorber. The adsorption of the ammonia is completed after 15 minutes. The reactor contents have cooled down to 95° C. during this time, and their ammonia content is only 0.06 kg (3.5 mol, i.e. 0.03 mol $NH_3$ per mole of tallow fatty nitrile used). The scrubber is then taken out of operation and the reactor contents are heated for the second hydrogenation up to 125° C., and pressurized at this temperature by means of hydrogen until the pressure remains constant at 18 bar, which is the case after 2.5 hours. A hardened tallow fatty amine is obtained having the following values:

primary nitrogen in equivalent percent: 97.5
non-primary nitrogen in equivalent percent: 2.5
residual content of tallow fatty nitrile in percent by weight: <0.1
iodine number: 3

We claim:

1. A process for the preparation of saturated primary fatty amines by hydrogenation of unsaturated fatty acid nitriles in the liquid phase in the presence of nickel catalysts or cobalt catalysts, which comprises a first reaction step in which the nitrile group of the fatty acid nitrile is hydrogenated to the primary amino group by reaction of the fatty acid nitrile with hydrogen in the presence of 0.1 to 10% by weight of the catalyst, relative to the fatty acid nitrile, and in the presence of 0.3 to 3 mol of ammonia per mole of fatty acid nitrile, at a temperature of 80° to 160° C. and a pressure of 10 to 50 bar, after which the ammonia content in the hydrogenation reaction mixture is reduced to a value of 0.1 to 0 mol per mole of fatty acid nitrile used, and a second reaction step in which the double bonds in the fatty acid nitrile are hydrogenated to saturated bonds by reaction of said reaction mixture having an ammonia content of at most 0.1 mol per mole of fatty acid nitrile used, with hydrogen at a temperature of 80° to 160° C. and a pressure of 1 to 40 bar.

2. The process as claimed in claim 1, wherein the hydrogenation in the first reaction step is carried out in the presence of 0.5 to 5% by weight of the catalyst, relative to the fatty acid nitrile, and in the presence of 0.5 to 1.5 mol of ammonia per mole of fatty acid nitrile, and at a temperature of 100° to 140° C., and a pressure of 20 to 40 bar, after which the ammonia content in the hydrogenation reaction mixture is reduced to a value of 0.05 to 0 mol per mole of fatty acid nitrile used, and in the second reaction step said reaction mixture having an ammonia content of at most 0.05 mol per mole of fatty acid nitrile used, is hydrogenated at a temperature of 100° to 140° C., and a pressure of 1 to 25 bar.

3. The process as claimed in claim 1, wherein nickel catalysts are used as the catalyst.

4. The process as claimed in claim 1, wherein the unsaturated fatty acid nitriles used are those having 8 to 22 carbon atoms.

5. The process as claimed in claim 1, wherein the unsaturated fatty acid nitriles used are mixtures of unsaturated fatty acid nitriles having 8 to 22 carbon atoms and up to 90% by weight of saturated fatty acid nitriles having 8 to 22 carbon atoms, percentages by weight being based on the sum of the weights of the unsaturated and saturated fatty acid nitrile.

6. The process as claimed in claim 5, wherein said amount of saturated fatty acid nitriles having 8 to 22 carbon atoms is up to 60% by weight, based on the sum of the weights of the unsaturated and saturated fatty acid nitrile.

7. The process as claimed in claim 5, wherein said unsaturated fatty acid nitriles have from one to three double bonds.

8. The process as claimed in claim 5, wherein said mixtures of unsaturated and saturated fatty acid nitriles have 12 to 18 carbon atoms.

* * * * *